United States Patent [19]

Copeland et al.

[11] 4,149,529

[45] Apr. 17, 1979

[54] PORTABLE THERMO-HYDRAULIC PHYSIOTHERAPY DEVICE

[75] Inventors: Thomas Copeland, Oregon; Terry L. Sandman; Dennis G. Mosiniak, both of Toledo, all of Ohio

[73] Assignee: Jobst Institute, Inc., Toledo, Ohio

[21] Appl. No.: 833,719

[22] Filed: Sep. 16, 1977

[51] Int. Cl.² .................... A61H 29/00; A61F 7/00
[52] U.S. Cl. ................................ 128/24.1; 128/400
[58] Field of Search ............... 128/399, 400, 402, 24.1, 128/24.2, 66, 64

[56] References Cited

U.S. PATENT DOCUMENTS

| | | | |
|---|---|---|---|
| 2,832,336 | 4/1958 | Davis et al. | 128/24.1 |
| 3,186,404 | 6/1965 | Gardner | 128/24.1 |
| 3,993,053 | 11/1976 | Grossan | 128/64 |

FOREIGN PATENT DOCUMENTS 2516443  10/1975  Fed. Rep. of Germany ........ 128/24 R

*Primary Examiner*—Lawrence W. Trapp

*Attorney, Agent, or Firm*—Wilson, Fraser & Clemens

[57] ABSTRACT

A portable apparatus for controllably cooling and variably, intermittently applying pressure to a portion of a body part of a mammalian organism comprising a liquid supply and control unit having means to store, circulate, cool, agitate, and pressurize a fluid and means to communicate via fluid communication means to a hydraulic appliance having a unitary body, with an unrestricted inlet port to receive the fluid, and an outlet port in association with a fluid flow retardation means secured to the interior surface of the outlet port. The reservoir in the supply unit is arranged with a heat exchanger immersed in the liquid and agitating means to avoid thermal stratification of the liquid. The reservoir is mounted in the supply unit with sufficient support to sustain the weight of a human and has an open top of sufficient dimensions to receive a human limb whereby the reservoir can be employed as a whirlpool bath. A cover is provided for the open top when the reservoir is not used as a whirlpool bath.

14 Claims, 4 Drawing Figures

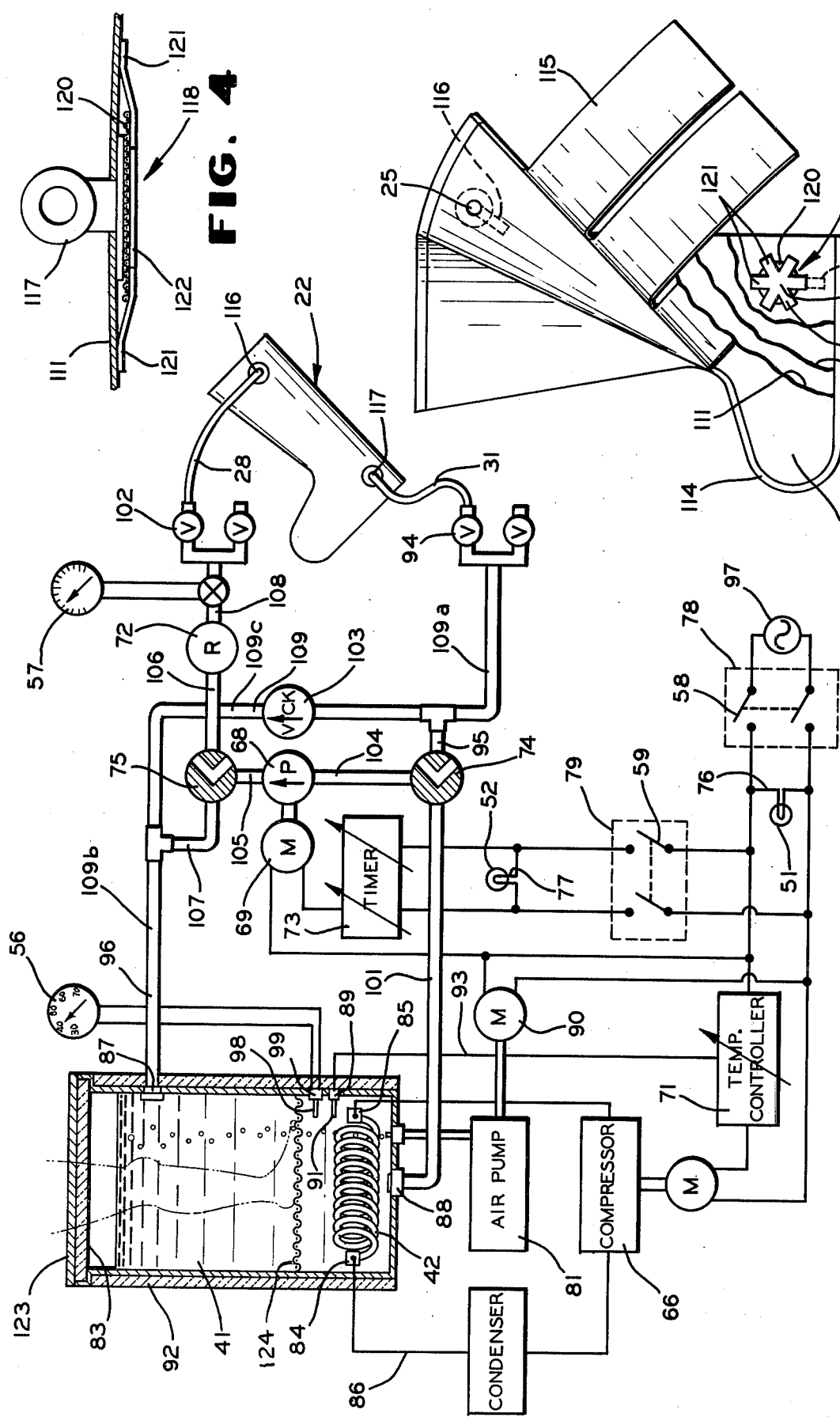

PORTABLE THERMO-HYDRAULIC PHYSIOTHERAPY DEVICE

BACKGROUND OF THE INVENTION

1. Field Of The Invention

Cold packing and pressure bandages are both well known medical management techniques. Cold packing is particularly well suited to the treatment of bruises, muscle strains, sprains and similar muscle, ligament and joint dysfunctions while pressure bandages and splints are used to control hemorrhage, temporarily secure pressure and antiseptic compresses while inhibiting the contamination of the injured surface by airborn bacteria and the like.

More conventional cold packing methods like ice bags, wet cloths, etc., can provide only short periods of relief for a number of reasons. Ice packs have to be periodically recharged requiring personnel time and the expense of purchase, transport, storage and replacement of large quantities of ice. Also, ice bags and wet cold cloths create a very damp cold which, while more tissue penetrating than dry cold is usually a more painful procedure to the patient than dry cold. These treatments also tend to dampen the surrounding area which has obvious contraindications in a sterile field or surgical theater. Additionally, recent medical advances in cryogenics and cryotherapy have indicated that lower temperatures than the operational range of ice packs and baths, usually 35° F. or so, are needed in some comprehensive medical management regimens. Along with these findings have come the need to produce ultracold methodology instrumentation. Additionally, these ultracold treatments have been seen to be less painful to the patient than damp cold treatments.

Concomitant advances in medical pressure usage techniques have disclosed the usefulness of intermittent variation in the pressure applied to a treated area. Traditionally, pressure bandages and splints have been of extremely simple design and usually able only to exert one fixed pressure. Any desired change in pressure was manually adjusted. Such adjusted pressures cannot be established accurately with ordinary procedures. While this technique of manual pressure variation is acceptable for crisis treatments, like acute cardiopulmonary or cardiothorasic events, the continued rotation and adjustment of pressure bandages and the like is not suited to routine treatment of subacute conditions since it would require the continuous presence of trained medical personnel.

Recently, chemical cold packs have been introduced. These devices are simply two or more chemical solutions or substances stored separately in a packet. Upon need an internal seal is broken, the substance mix and the reaction produces a strongly endothermic reaction thereby cooling the cold pack to a single, preset at the manufacture point, low temperature. The devices are typically used in remote site use, like a paramedical team, and suffer also from some serious disadvantages in general use. First, these packs are extraordinarily expensive, have only a one use lifetime, have a single nonadjustable temperature and exert cold only for a short period of time.

DESCRIPTION OF THE PRIOR ART

Heretofore, a number of devices and systems have been employed to impose heat or cold and/or pressure on parts of a mammals. Rinkes et al, U.S. Pat. No. 2,272,481 of Feb. 10, 1942 discloses a chamber adapted to receive a limb such as an arm and having liquid input and exit fittings coupled in a closed system to a reservoir and pump. Liquid is guided in a helical path around the limb by ribs on the interior of the chamber wall and a thermostatically controlled heater in the reservoir establishes a predetermined temperature in the treating liquid. This provides a wet bath and massage of the limb.

Miller U.S. Pat. No. 2,531,074 of Nov. 21, 1950 discloses an appliance for a dry massage at a controlled temperature by applying water of controlled temperature in a controlled sequence at alternately high and low pressures to a plurality of adjacent chambers of flexible walled material is suggested that the water can be either heated or cooled.

Chessey U.S. Pat. No. 2,726,658 of Dec. 13, 1955 shows a system including a coolant control and supply unit and a liquid impervious appliance receiving the coolant and applicable as a pad to a body portion of a mammal. It includes a mechanical refrigeration system in the supply unit controlled thermostatically by the temperature of the coolant which is maintained in part by intermittent operation of the refrigerator to cool the coolant in a heat transfer tank containing a heat exchanger. Coolant is driven through the appliance by a motor which is controlled by a thermostat responsive to the temperature of the coolant exiting the appliance.

Gardner U.S. Pat. No. 3,186,404 of June 1, 1965 includes an appliance, illustrated for human limbs, in the form of a double walled envelope for limbs which can be filled with fluid to impose pressure on the enclosed limb. It is suggested that a continuous or intermittent flow of pressurized air can be passed through the appliance for cooling or for heating at a selected pressure, the animal part therein.

Pressure can be derived from refrigerant when it is utilized directly in the appliance as disclosed in Roslonski U.S. Pat. No. 3,871,381 of Mar. 18, 1975 wherein a refrigerant source is coupled to a pad containing refrigerant passages and a relief valve which bleeds the refrigerant to atmosphere. Within the limits of the passage geometry and gas pressure of the expanded refrigerant some pressure is available from such systems until the supply of refrigerant is exhausted.

Mechanical cooling from a system including a portable mechanical refrigerator coupled to an evaporation coil in the general shape of the body portion to be cooled and covered by a flexible jacket or sleeve is shown in Saunder et al. U.S. Pat. No. 3,916,911 of Nov. 4, 1975. Only binding pressure is imposed in such arrangements.

An object of this invention is to improve apparatus for constantly or intermittently applying adjustable pressure to a body part and/or sustaining an adjustably selected temperature on the part through the medium of a liquid.

Another object is to combine a whirlpool bath with a temperature controlled intermittent compression system for the treatment of body parts.

A further object is to facilitate the control of pressure imposed by a circulating liquid on an appliance for body parts.

SUMMARY OF THE INVENTION

The above objectives are achieved in the present invention by a system for the medical management of a body portion of a mammal comprising a modular liquid control station capable of storing, circulating, cooling and agitating a liquid and controlling the temperature and/or pressure of the fluid for delivery to an appliance. The liquid is passed through a circuit to a hydraulic appliance which receives the liquid into an inlet port freely and allows the forced flow of the liquid through a body, having a hollow interior cavity. The liquid flow is retarded at the outlet port by a liquid retardation means of limited liquid porosity, this retardation means when used in concert with the force applied via the liquid circulation and pressurization means of the modular control station results in the precisely controlled pressurization of the hydraulic appliance. A duty cycle timer allows the programmed intermittent pressurization of the appliance by operation of a pump for the liquid while the temperature control system regulates the temperature of the liquid and thus the hydraulic appliance. The temperature range is typically maximized at 75°-80° F. with a lower limit well below the effective operational range of an ice bath, typically on the order of 35° F.

BRIEF DESCRIPTION OF THE DRAWINGS

Principles and advantages of the invention will be understood from the following detailed description of an embodiment of the invention as illustrated by the accompanying drawings, in which:

FIG. 2 is a cross section of the storage unit assembly utilized as a whirlpool bath with the coolant and electrical control circuits shown schematically;

FIG. 3 is a side view of the hydraulic appliance for receiving the fluid with portions broken away to reveal construction details; and FIG. 4 shows a cross sectional view of the flow restrictive outlet of an appliance.

DESCRIPTION OF THE PREFERRED EMBODIMENT

Figure 1:
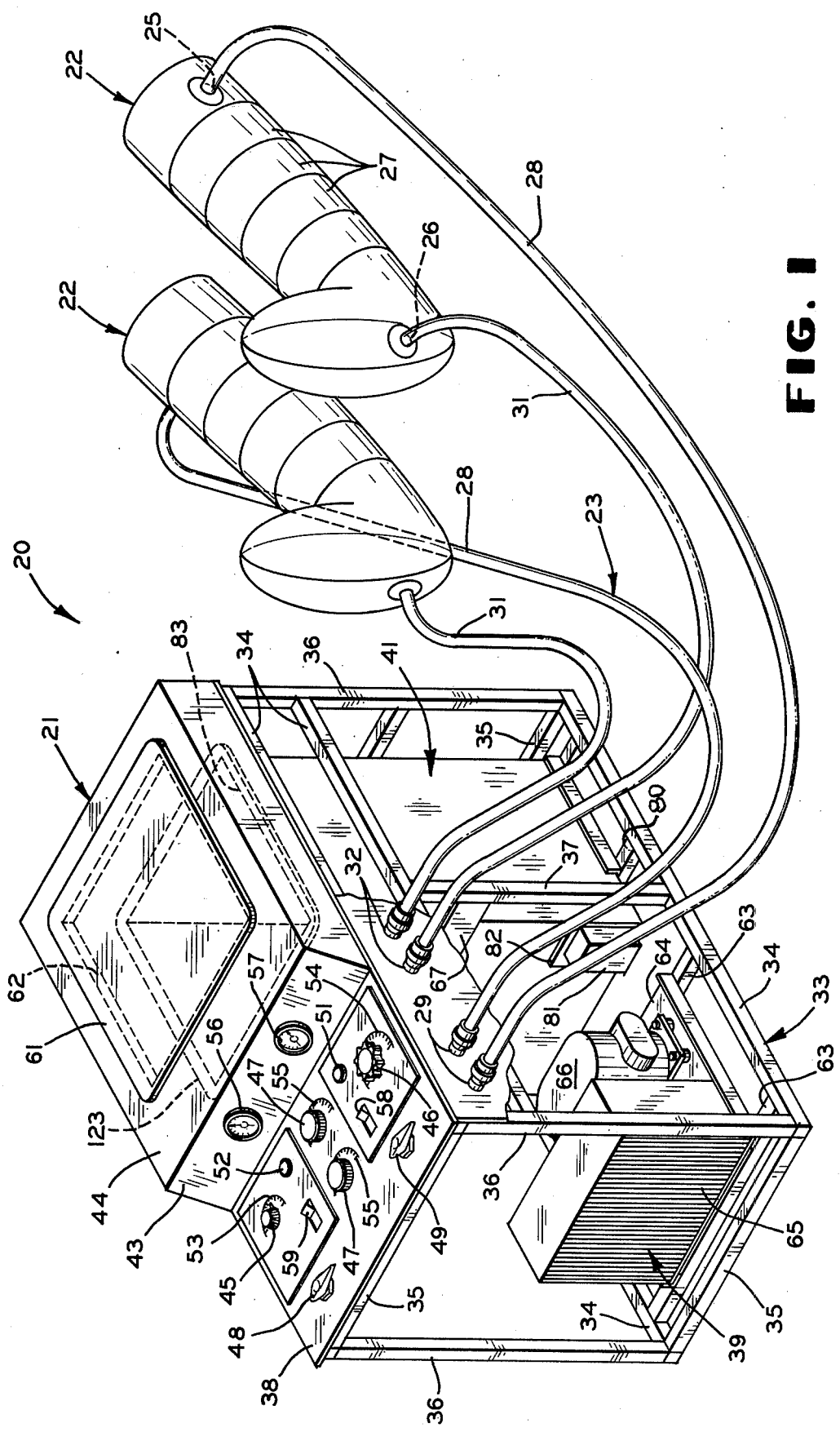
FIG. 1 is a perspective view of the system of the invention with portions removed or broken away to reveal interior structure and other interior structure represented in phantom, only portions of the fluid connections are shown.

Referring initially to FIG. 1, there is shown the general apparatus 20 which includes a modular fluid control station 21 which communicates with the hydraulic appliance 22 through the liquid communication means 23. The hydraulic appliance 22 comprises a double walled envelope for liquid which forms a hollow unitary body 24 with an inlet port 25 integral with the unitary body 24, an outlet port 26, also integral with the unitary body 24, and securing means 27 to hold the appliance 22 in place on the body part.

The appliance 22 is connected to the fluid control station 21 through liquid communications means 23, in the form of flexible hoses including liquid supply hoses 28 from liquid outlets 29 on station 21 and liquid return hoses 31 to liquid inlets 32. The ends of hoses can be fitted with quick disconnect hose couplings which are adapted to mate with the quick disconnectors on the station 21.

The fluid control station 21 comprises a housing, side cover panels of which have been removed, built up on a base frame 33 made up of horizontal side and end beams 34 and 35 and vertical corner and intermediate columns 36 and 37. As seen in FIG. 1, mounted on the sides of the station 21 are the inlets and outlets 32 and 29 for the liquid to be circulated in the appliance. The invention is designed to accommodate two appliances 22 simultaneously, there being two inlets 32 and outlets 29 on the station 21.

The housing is closed at the upper edges by a top panel 38 upon which and through which are mounted various control elements to be discussed in detail later.

Fluid control station 21 contains a refrigeration system 39, a coolant reservoir 41, an evaporator coil 42 of system 39 in the bottom of reservoir 41 and the control and pumping means for the coolant. Externally accessable controls and indicators appear on the top 38 of the housing for the station and the inclined panel 43 joining a raise top section 44 with main top panel 38. Since the control station is arranged to apply coolant under pressure to the appliance intermittently and at adjustable controlled pressures and temperatures, top panel 38 displays a temperature control knob 45, a pressure regulator control knob 46, a timer control knob 47 and two valve control knobs 48 and 49 for establishing the desired coolant paths within the coolant circuit. The indicators on the top panel 38 are a main pilot lamp 51, a timer pilot lamp 52, calibrated scales for the settings of the control knobs for temperature 53, pressure 54 and time cycle 55. Inclined panel 43 has a temperature gauge 56 and a pressure gauge 57. Control switches 58 and 59 for the main electrical power supply and the timer respectively are mounted on the main top panel 38. A removable cover 61 is provided for an aperture 62 on the raised top panel section 44 to offer access to the coolant reservoir 41 and enable it to be used as chilling and/or whirlpool bath for limbs inserted through the aperture 62 and into the reservoir.

Internally, the control station has its operative elements mounted on the base frame 33 either directly or on supplemental cross beams or internal panels mounted on the cross beams or main frame. Many of the elements are hidden in FIG. 1 and are schematically illustrated in FIG. 2. Cross beams 63 extending between side beams 34 support a panel 64 for the refrigeration system condenser 65 and motor-compressor 66. Intermediate columns 37 have a cross beam 67 on which is mounted pump 68 and its motor 69 together with fittings and support clamps for much of the internal plumbing shown only in schematic form in FIG. 2.

Top panel 38 supports on its under side, so that they are not visible in FIG. 1, many of the elements shown schematically in FIG. 2. These elements are supported by threaded couplings around the control shafts connected to the control knobs in locations below those knobs and by conventional screw mounted brackets. The elements include temperature controller 71, pressure regulator 72, timer 73, valves 74 and 75, pilot lamp sockets 76 and 77, and switch housings 78 and 79.

Stratification of the chilled coolant in reservoir 41 is avoided by bubbling air through the coolant. Air pump 81 for the bubbler is mounted in panel 82 secured to intermediate column 37.

Cross beams 80 extending between side beams 34 have angle iron stringers spanning the space between them to form a cradle for the bottom of reservoir 41.

Connector fittings between the internal plumbing and the hoses 28 and 31 are mounted on side panels for the station. A sight glass, not shown, can be provided to indicate the liquid level in reservoir 41 at a side panel and suitable vents can be provided to afford adequate ambient air circulation through the condensor 65.

The liquid control station 21 functions in four principal modes of liquid transfer, a reservoir fill, an appliance fill, a reservoir circulate, and an appliance circulate mode. It also establishes any temperature selected in a range for the coolant, a maximum selected pressure within a range for the appliance, and a duty cycle of time the appliance is subjected to pressure and a time the appliance is relieved of pressure.

Reservoir 41 typically is a tank of polymeric material such as polyethylene having an open upper end 83 and suitable fittings 84 and 85 for the passage through its walls in liquid tight relationship of the refrigerant tubing 86 between evaporation coils 42 and compressor 66 and condenser 65. Inlet and exit fittings 87 and 88 on the tank wall and bottom respectively for the coolant within the tank are coupled to the remainder of the liquid circuit as by hoses and a fitting 89 for a thermal sensor such as a thermocouple 91 electrically coupled to temperature controller 71 also passes through the reservoir wall. Thermal insulation in the form of sheets 92 which may be polymeric foam are secured around the outer walls of the reservoir and in the cover 61 and are pierced where the fittings and fluid conduits to which they are connected pass.

The controls discussed include the main on-off switch 58 which activates all electrical components by energizing the supply circuits and directly activates the motor 90 for the air pump and the electrical refrigeration components including temperature controller 71 and through it the motor for compressor 66. Pump on-off switch 59 activates the components associated with pumping liquid through the hydraulic appliance and filling and draining the tank including dual timer 73 and pump motor 69. Pressure regulator 72 controls the pressure applied to the appliance. Temperature control 71 provides an adjustable control of coolant temperature and maintains that temperature as sensed by thermal sensor which supplys a control signed on line 93 to control 71. Dual timer 73 controls the "on" time and "off" time of pump 68 to control the duty cycle of intermittent pressure imposed on the appliance. Flow control valves 74 and 75 establish the paths of coolant flow under the impetus of the pump 68.

The liquid circuit can be set up to fill the tank from a suitable container (not shown). Advantageously an antifreeze solution is added, typically, one gallon of antifreeze for fourteen gallons of water. The mixture is drawn from the container through a return hose 31 from an appliance by disconnecting the hose from the appliance and opening the appliance return valve 94 (this may be a valve in the fitting which opens when the hose 31 is connected), while valve 74 is set to couple suction line 95 to pump 68 and valve 75 is set to couple pump 68 to tank return line 96. Both the main switch 58 and the timer control switch 59 are closed to couple source 97 through timer 73 to pump motor 69. The refrigeration system is not needed at this time so the temperature controller 71 should be set high. Dual timer 73 should be operated with a long on interval, for example 180 seconds "on" and 5 seconds "off" to cause the pump to operate a preponderance of the time. Coolant thus is pumped from hose 31 through valve 94 to the control station 21 and within the station passes through suction line 95, valve 74, pump 68 valve 75, return line 96 to inlet fitting 87 and into reservoir 41. When the desired level of fluid has been introduced into the reservoir, the filling can be terminated by opening switch 58.

After use, the same circuit setting employed to fill the reservoir can be used to empty the appliance. In this case the return hose 31 or hoses 31, where two appliances are in use, are coupled to their respective appliance 22.

The coolant is brought to the desired temperature by operating the refrigeration system and bubbler. Main switch 58 is closed and the desired temperature setting made on temperature controller 71 so that the compressor operates until the signal from thermal sensor 91 causes controller 71 to interrupt the circuit to the compressor-motor 66. The coolant can then be internally circulated to assure that it is at a uniform temperature and that temperature can be read on temperature gauge 56 as actuated from thermal probe 98 which is located in the reservoir by a probe fitting 99 in the wall. Internal circulation of coolant should be continued until a stable temperature is indicated.

An internal circulation of coolant is set by connecting exit line 101 through valve 74 to pump 68 while valve 75 is connected to return line 96.

Circulation through the appliance 22 involves closing main switch 58 to supply electrical power and timer control switch 59 while the desired temperature setting is made on temperature controller 71 and the "on" interval and "off" interval are set on dual timer 73. Coolant is drawn from reservoir 41 through fitting 88 and exit line 101 to valve 74 coupling line 101 to pump 68. It is then passed from pump 68 through valve 75 to regulator 72, set to the desired pressure, and thence through feed valve 102 to supply hose 28. With these settings of valves 74 and 75 a return path from appliance 22 is through return hose 31 return valve 94, suction line 95, check valve 103 and return line 96 to fitting 87 and the tank.

The return circuit is relatively unobstructed and provides only limited means to develop a back pressure within the appliance. Thus the pressure in the appliance will not reflect the pressure set at the regulator and great volumes of coolant will be required to be pumped by pump 68 to satisfy some higher settings of regulator 72. This deficiency is overcome by a constriction in the exit from the appliance which is of a nature to concentrate the pressure drop in the circuit from the regulator to the reservoir at the appliance exit and thus cause the appliance internal pressure to closely approximate the setting of the regulator. This enables appliances of different size and thus having different internal volumes to be coupled to the fluid control station 21 and to accurately reflect the regulator pressure settings.

It will be noted that the pressure regulator 72 is only in the liquid circuit portion including that for circulating coolant through the appliance or appliances. Thus the remainder of the circuit can be essentially unconstricted and free flowing for the reservoir fill mode, the appliance empty mode and the internal circulate mode. The combination of the pressure regulator and appliance flow constraint at its exit imposes a back pressure load on the system other than the normal flow resistance of the liquid circuit elements only when in the appliance circulate mode and even then the appliance to reservoir return portion of the liquid circuit is unrestricted and permits the appliance to bleed its pressure down when the pump is turned off, thereby providing the intermittent compression with the same fluid providing the thermal treatment.

In practice it has been found that a pair of appliances for treating human legs with a liquid having a predetermined temperature and subject to regular periods of imposed pressure while pump 68 is operating, and relieved pressure while pump 68 is dormant, can be supplied by about fifteen gallons of liquid through half inch hose lines, valves, and fittings by a pump of five gallons per minute capacity. The system is equally effective for low volume requirements such as an appliance to an ankle, knee or wrist. Further, the flow in the liquid circuit is relatively unrestricted except when operated in the mode directing liquid through the regulator and appliance with its flow impeding constriction. Portions of the circuit are used for a multiplicity of operating modes. within the station the circuit includes liquid issuing and receiving fixtures 29 and 31, a first two way valve 74 to couple alternate liquid sources to the pump 68 and a second two way valve 75 to couple the pump output to the reservoir 41 or appliance 22. A first input line to valve 74, reservoir exit line 101, enables liquid to be drawn from the reservoir for all but the appliance empty mode. A second input line to valve 74, the suction line 95, draws liquid from the appliance for the appliance empty mode. All modes pass the liquid through an output line 104 from valve 74 to pump 68. Pump delivery line 105 carries all liquid in all modes to valve 75. In the appliance fill and circulate modes, liquid is passed from valve 75 to regulator 72 through a first output line 106. In the internal circulation and appliance, empty mode liquid is passed from valve 75 through a second output line, line 107 and tank return line 96, to reservoir 41. Flow from the regulator 72 to issuing fixture 29 is through line 108 for the appliance fill and circulate modes. A liquid receiving line 109 from receiving fixture 32 to reservoir 41 has a first portion 109a merged with a portion of suction line 95, a second portion 109b merged with a portion of tank return line 96 and a third portion 109c including check valve 103 so that it returns liquid from the appliance to the reservoir in the appliance circulate mode using portions of lines also employed in all other modes.

FIGS. 3 and 4 disclose a typical appliance construction. Numerous forms of appliances are applicable to this system wherein they offer an envelope for liquid which can be applied to a body portion of a mammal such that the application of liquid under pressure causes a flexible, liquid impervious, wall adjacent the body portion to be pressed against that body portion. In FIG. 3 a boot is shown made up of an outer wall of fabric 111 which is sealed along its margins to an inner wall of fabric 112 to form a flexible, liquid impervious envelope. The boot is provided with a foot 113 which is closed along its marginal seam 114 along the bottom and over the toe and instep. The leg region is open along the front and provided with a number of binders 115 of webbing which can be secured around the leg region to constrain the appliance against ballooning. A single compartment for pressurized liquid coolant thus encompasses the patient's foot and leg. Coolant is introduced through the inlet fitting such as a hose coupling 116 to which supply hose 28 is connected, passes through the appliance interior and exits at exit fitting 117 which may also be a hose fitting. In order to develop the internal pressure, a liquid flow constriction 118 is provided at the exit port 26 communicating with fitting 117. This constriction is a fiberous pad 120 retained on the inner face of the wall contiguous to port 26 by a spider 119 which can be of fabric of the type employed for the walls of the appliance and is bonded at the ends 121 of the spider legs to those walls. Pad 120 has sufficient thickness to permit lateral flow of the coolant therethrough and to space the body portion 122 of the spider 119 from the appliance walls adjacent port 26. Coolant flows between the legs of the spider and through the pad to the port 26 and the port is maintained open by the thickness of the pad even when return hose 31 is under suction for emptying the appliance. The pad thickness and overlying spider also prevents the opposed wall of the appliance from collapsing on port 26 to close it.

Pad 120 is formed advantageously of a three dimensional synthetic textile made by weaving two different fibers along the length of the fabric and another across the width. One of the longitudinal fibers shrinks more when temperature-processed than the other to cause the fabric to pucker and develop a thickness. Polyethylene is a suitable shrinkable fiber and the other fibers can be polypropylene, nylon or Saran monofilament. In practice a pad of about three inch diameter is retained within a spider of about a five inch span having a body portion 122 of about one inch diameter.

Another aspect of the present system is that it provides a wet temperature controlled treatment of limbs utilizing the coolant reservoir 41 as the wet treatment tub. Such use can be made of the system in the internal circulation mode as well as in the appliance circulation or intermittent compression-thermal treatment mode. Cover 61 is removed to expose aperture 62 in the raised top section 44 of station 21. A tank cover 123 with suitable insulating lining for closing the upper end 83 of reservoir is removed, thereby exposing the coolant free surface.

An arm or leg to be treated can be inserted through open top 83 of reservoir and immersed in the coolant. Coolant is circulated by the placement of inlet fitting 87 in the reservoir wall near the free surface of the coolant and exit fitting 88 at the bottom. It is enhanced by the bubbler action of air pump 81. Contact by a hand or foot with the evaporator coils 42, forming the heat exchanger between the refrigerant and coolant, is avoided by a protective screen 124 secured to the reservoir walls above the coils 42 and the thermal sensors 91 and 98.

While the described system for temperature and intermittent compression treatment in a dry appliance and as a temperature and bath treatment has been described with respect to a cooled liquid system it is to be appreciated that a heated liquid system might also be used. The invention lends itself to many varients accordingly it is to be understood that the disclosure is to be read as illustrative and not in a restrictive sense.

What is claimed is:

1. A system for applying liquid pressure to an animal body portion comprising a liquid control station; a liquid reservoir in said station; a liquid pump in said station; a liquid flow circuit including said reservoir and pump and having a plurality of paths within said station; means for selectively establishing each of a plurality of liquid flow paths each including said pump and said reservoir and each providing relatively unrestricted flow of said liquid; a liquid pressure regulator, a liquid conduit from said flow circuit to said regulator; an appliance having a closed envelope of flexible liquid impervious material having a liquid inlet port and a liquid exit port and adapted to be constrained against said animal body portion; a liquid conduit from said regulator to said liquid inlet port of said appliance; a liquid conduit from said liquid exit port of said appliance to said liquid flow circuit; and a liquid flow restricting means within said appliance and between the appliance interior and said exit port whereby hydraulic pressure established by said regulator is imposed on said appliance by restricting flow therefrom while the liquid flow from said appliance to said reservoir through said liquid conduit from said appliance and said liquid flow circuit is relatively unrestrained.

2. A system according to claim 1 wherein said regulator is adjustable to adjust the pressure of the liquid imposed on said appliance.

3. A system according to claim 1 wherein said liquid flow restricting means is a fibrous pad overlying said exit port.

4. A system according to claim 3 wherein said pad is a three dimensional textile.

5. A system according to claim 4 wherein said pad has a thickness permitting lateral flow of liquid therethrough and sufficient to maintain the walls of said envelope overlying said exit port spaced for the walls contiguous to said exit port to accommodate liquid flow from said port.

6. A system according to claim 3 including a spider of fabric overlying said pad and having spaced legs extending beyond said pad and bonded to the interior of the wall of said envelope adjacent said exit port.

7. A system according to claim 1 including a timer to control operation of said pump intermittently whereby liquid pressure is intermittently applied to said body portion.

8. A system according to claim 7 wherein said timer is adjustable as to "on" time and "off" time.

9. A system according to claim 1 including a heat exchanger in said reservoir to maintain a predetermined temperature in said liquid.

10. A system according to claim 9 wherein said reservoir includes an open top adapted to receive a limb for immersion thermal bath treatment.

11. A system according to claim 10 including a liquid pervious barrier located between said open top of said reservoir and said heat exchanger to prevent contact of a portion of said limb with said heat exchanger.

12. A system according to claim 9 including means to admit gas to the lower portion of said reservoir to agitate said liquid by the flow of bubbles and avoid thermal stratisfaction of said liquid.

13. A system according to claim 1 wherein said liquid flow circuit includes a liquid issuing fixture; a liquid receiving fixture a first two way valve; a first input line from said reservoir to said first valve; a second input line from said fluid receiving fixture to said first valve; an output line from said first valve to said pump; a second two way valve; a pump delivery line between said pump and said second two way valve; a first output line from said second valve to said regulator; a second output line from said second valve to said reservoir; a liquid issuing line from said regulator to said liquid issuing fixture; and a liquid receiving line from said receiving fixture to said reservoir.

14. A system according to claim 13 wherein a first portion of said liquid receiving line is merged with said second input line to said first valve and a second portion of said liquid receiving line is merged with said second output line from said second valve; and including a check valve in said liquid receiving line in a third portion thereof between said first and second portions, said check valve passing liquid toward said reservoir.

* * * * *